United States Patent [19]

Cobo et al.

[11] Patent Number: 5,174,279

[45] Date of Patent: Dec. 29, 1992

[54] IRIS RETRACTOR FOR USE IN OPERATIONS ON THE EYE OF A LIVING CREATURE

[75] Inventors: Michael Cobo, Durham; Dyson Hickingbotham, Bahama; Eugene de Juan, Jr., Durham, all of N.C.

[73] Assignee: Duke University Medical Center, Durham, N.C.

[21] Appl. No.: 708,943

[22] Filed: May 31, 1991

[30] Foreign Application Priority Data

Mar. 6, 1991 [CH] Switzerland .......................... 679/91

[51] Int. Cl.⁵ .............................................. A61B 17/02
[52] U.S. Cl. ....................................... 128/20; 606/107
[58] Field of Search ............................ 128/17, 18, 20; 606/107, 151, 166, 191, 198, 201

[56] References Cited

U.S. PATENT DOCUMENTS

| | | | |
|---|---|---|---|
| 3,542,015 | 11/1970 | Steinman | 128/20 |
| 4,037,589 | 7/1977 | McReynolds | 606/107 |
| 4,257,406 | 3/1981 | Schenk | 128/20 |
| 4,387,706 | 6/1983 | Glass | 606/107 |
| 4,621,619 | 11/1986 | Sharpe | 128/20 |
| 4,991,567 | 2/1991 | McCuen, II et al. | 606/107 |

Primary Examiner—Cary E. O'Connor
Attorney, Agent, or Firm—Egli International

[57] ABSTRACT

An iris retractor for use in operating on the eye of a living creature is proposed, by means of which the iris is drawn outwards for widening the pupil and is held at the outer edge, which is essentially formed by the transition from the cornea to the sclera.

The iris retractor essentially comprises a suspended part having a hook portion and a guide part and on which a platelet-like clamping part is displaceable relative to the hook portion.

10 Claims, 2 Drawing Sheets

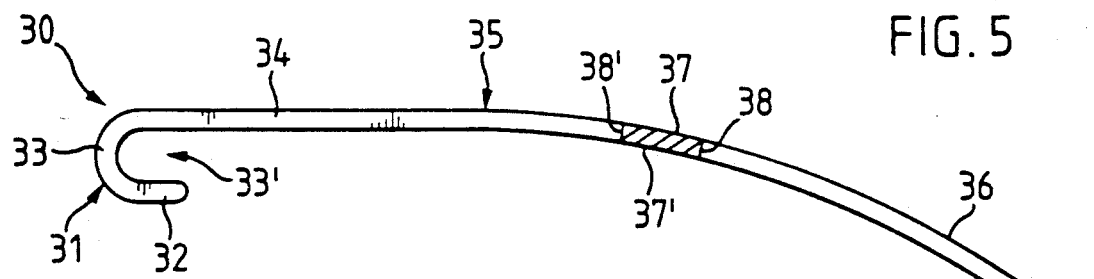
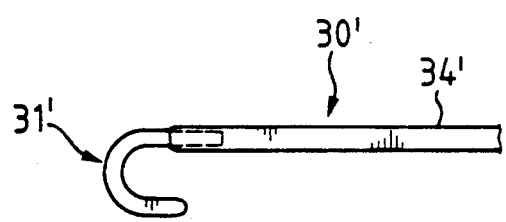
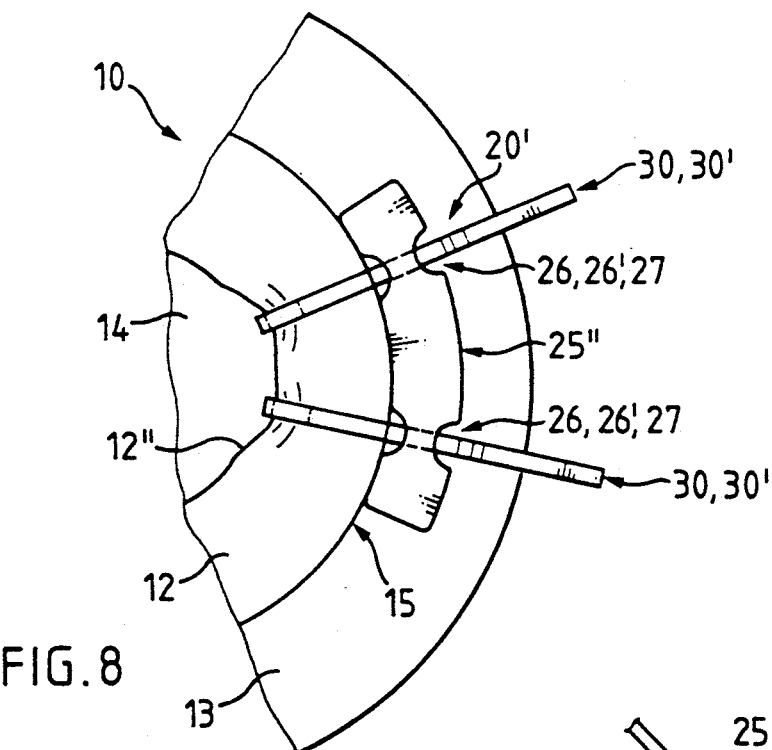
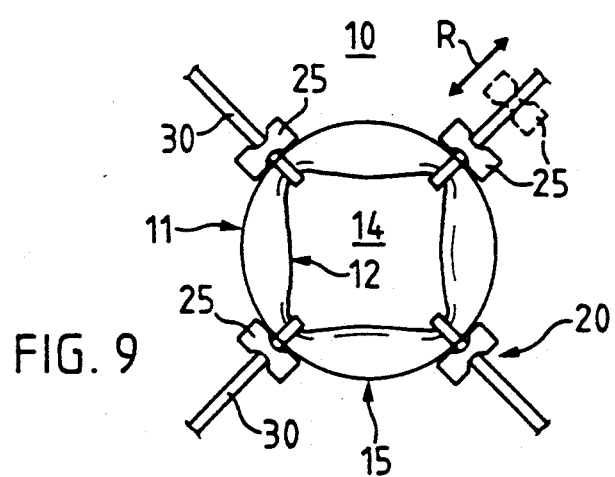

IRIS RETRACTOR FOR USE IN OPERATIONS ON THE EYE OF A LIVING CREATURE

BACKGROUND OF THE INVENTION

1. Field of the Invention

The invention relates to an iris retractor for use when operating on the eye of a living creature, with a suspended part provided with a hook portion appropriate for retracting the iris and on which is arranged a clamping part displaceable relative to the hook portion and by means of which the iris retractor can be fixed together with the retracted iris region approximately on the outer edge of the cornea.

2. Discussion of the Prior Art

The American Journal of Ophthalmology, vol. 110, p 577 of Nov. 15, 1990 discloses an iris retractor of the aforementioned type, which has a hook-like suspended part and a cylindrically constructed clamping part displaceably arranged thereon. The suspended part made from a rod or wire has the hook or retractor at one end and transversely with respect to the latter is provided at the other end a web bent upwards roughly at right angles for holding the iris retractor. As a result of its construction the known iris retractor cannot be precisely fixed. In ophthalmic surgery the problem often occurs that the pupil cannot be widened in a medicamentous manner to a sufficient extent for the necessary viewing and lighting requirements of the surgeon and consequently a reliable intervention on the eye is not ensured.

SUMMARY OF THE INVENTION

The problem of the present invention is to provide an iris retractor making it possible to ensure precise handling during insertion and removal, as well as keeping to a minimum the surface pressure on the sensitive part of the iris, thereby largely preventing any iris laceration.

According to the invention this problem is solved in that the suspended part is constructed as a rod-like profile body and has at least two parallel, longitudinally oriented guide surfaces and/or guide webs arranged orthogonally thereto and that the clamping part is constructed roughly as a rectangular platelet, which is provided with at least one recess passing through the cross-section in the direction of the two clamping part longitudinal sides and corresponding to the profile cross-section of the suspended part.

The inventive iris retractor inter alia has the advantage that for surgical intervention on the cornea it is only necessary to have relatively small incisions or punctures which automatically close following the operation and consequently a time-consuming stitching is either unnecessary, or is only necessary in rare cases.

BRIEF DESCRIPTION OF THE DRAWINGS

The invention is described in greater detail hereinafter relative to non-limitative embodiments and the attached drawings, wherein show:

FIG. 5 The suspended part for the iris retractor in elevation and on a larger scale.

FIG. 6 A front portion of another embodiment of the suspended part according to FIG. 5.

FIG. 8 A portion of the eye shown in plan view with a second embodiment of the iris retractor.

FIG. 9 The eye shown in plan view with several distributed iris retractors.

DESCRIPTION OF THE PREFERRED EMBODIMENTS

Figure 1:
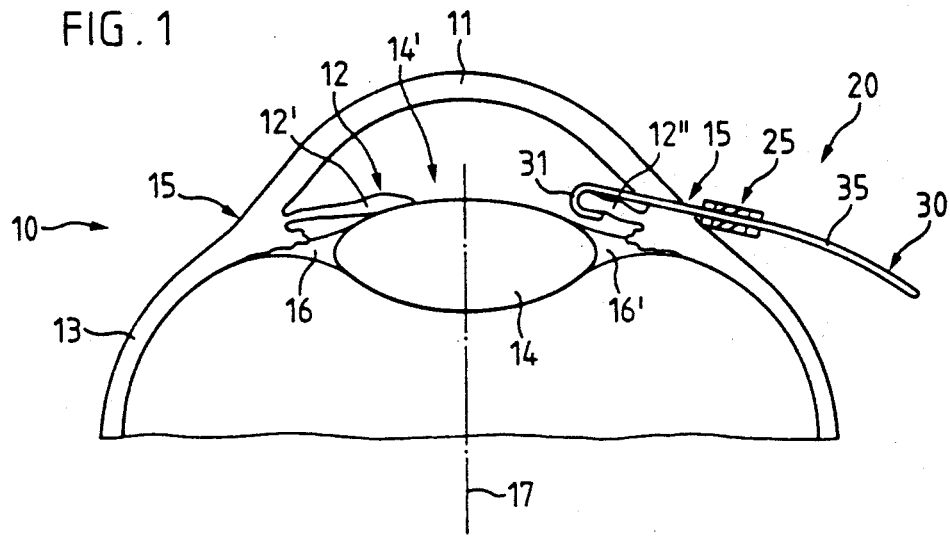
FIG. 1 An eye shown diagrammatically and in cross-section, in which one region of the iris is retracted with a correspondingly constructed iris retractor and is held on the outer edge of the cornea.

In order to illustrate the invention FIG. 1 shows an eye 10 in diagrammatic cross-section and it is possible to see the cornea 11, the iris 12 with the regions 12' and 12'', the sclera 13, the lens 14, the pupil 14' and the zonulas 16, 16'.

Figure 2:
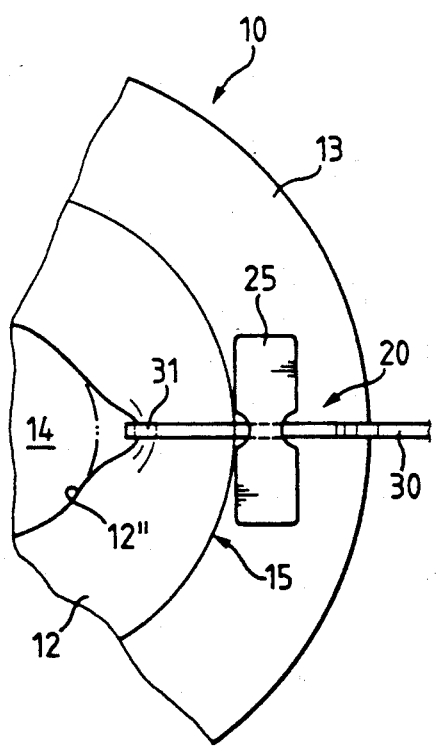
FIG. 2 A portion of the eye shown in plan view with the iris region retracted by means of the iris retractor.

It is also possible to see an iris retractor 20 by means of which e.g. the region 12'' of the iris 12, as shown in FIG. 2, is drawn outwards relative to the theoretical line of vision 17 of the eye 10 and is held approximately at the transition 15 between the cornea 11 and the sclera 13. The iris retractor 20 essentially comprises a platelet-like clamping part 25, shown in section in FIG. 1, and a suspended part 30, which passes through the cornea 11 and is suspended on the iris region 12''.

FIG. 2 is a diagrammatic plan view of a portion of the eye 10 with the iris region 12'' retracted by means of the iris retractor 20. The retractor 20 is held by the clamping part 25 arranged displaceably on the suspended part 30 and engaging at the transition 15 of the eye 10. The clamping part 25 is made from corresponding flexible material, so that the side facing the transition 15 can adapt to the arcuate transition 15 (not shown).

The construction and further variants of the clamping part 25 and the suspended part 30 for the iris retractor 20 are described hereinafter by means of FIGS. 3 to 8. The platelet-like clamping part 25 shown in plan view in FIG. 3 and in side view in FIG. 4 is penetrated by a roughly slot-like opening 27 oriented transversely to its longitudinal direction. In the vicinity of the opening 27 the clamping part 25, which is preferably rectangular in profile cross-section, is provided with two correspondingly arranged recesses 26, 26'. The recesses 26, 26' are e.g. arcuate, so that the side walls are essentially subdivided into two portions 28, 28' and 29, 29', which ensure an optimum adaptation of the corresponding side wall to the transition contour 15 of the eye 10. In addition, the two recesses 26, 26' lead to a reduction of the clamping part cross-section and the length of the slot-like opening 27, so that the friction of the suspended part 30 which can be slid through the opening 27 is reduced.

The clamping part 25 is essentially used for positioning and fixing the suspended part 30 at the transition 15 of the eye 10 and, as stated, in the fixed state the side wall portions 28, 28' or 29, 29' of the clamping part 25 facing the transition 15 or the cornea 11 adapt in not shown manner to the contour of the latter due to the recess 26 or 26' and the flexibility.

Figure 3:
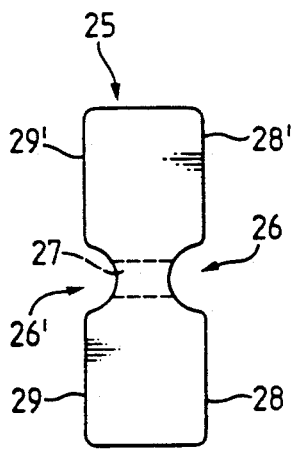
FIG. 3 A clamping part for the iris retractor shown in plan view and on a larger scale.
Figure 4:
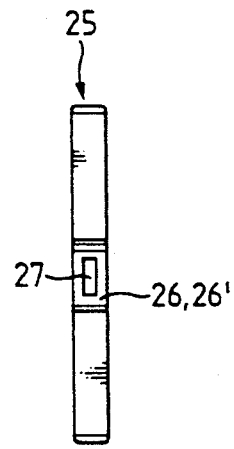
FIG. 4 The clamping part of FIG. 4 in elevation.
Figure 7:
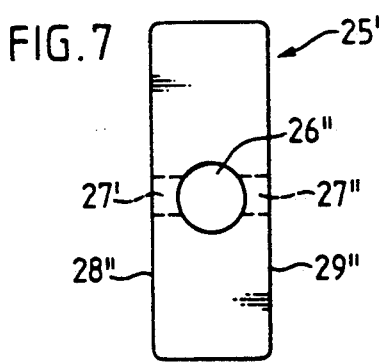
FIG. 7 A second embodiment of the clamping part for the iris retractor shown in plan view.

FIG. 7 shows another embodiment of the clamping part 25' shown in plan view, in which in place of the lateral recesses 26, 26' in FIG. 3, there is a single, central recess 26''. The latter is connected to two corresponding openings 27' and 27" through which is passed the suspended part 30.

In a not shown embodiment of the clamping part 25 or 25', one of the two side walls can be provided with an arcuate shape corresponding to the transition 15 or the contour of the cornea 11 of the eye 10.

The clamping part 25 or 25' is roughly constructed as a rectangular platelet, which is provided with at least one recess 27 (FIGS. 3 and 4) or 27', 27" (FIG. 7) passing through the cross-section in the direction of the two clamping part longitudinal sides 28, 29 (FIG. 3) or 28"', 29"' (FIG. 7) and constructed corresponding to the profile cross-section of the suspended part 30.

The clamping part 25 or 25' is made from a suitable, corresponding flexible plastic, which also has optimum sliding characteristics for the substantially forceless sliding through of the suspended part 30. The clamping part 25 or 25' is preferably made from silicone (silicone rubber).

The suspended part 30 shown in elevation in FIG. 5 has a hook portion 31 bent over once in hairpin-like manner and a guide part 35 shaped onto it. In a preferred embodiment the guide part 35 has a portion 34 shaped substantially straight onto the hook portion 31 and an approximately arcuate portion 36. Onto the straight portion 34 is shaped a hook portion 31 provided with a bow 33 and a leg 32 arranged with a roughly parallel spacing 33' with respect to the portion 34.

The suspended part 30 is constructed preferably as a rod-like profile body and has at least two parallel, spaced, longitudinally oriented guide faces 37, 37' and/or guide webs 38, 38' arranged orthogonally thereto and on which is displaceably guided in the longitudinal direction of the suspended part 30 the said clamping part 25.

In profile cross-section the suspended part 30 can be square or, as shown in section in FIG. 5, rectangular. A preferred and in profile cross-section rectangular, relatively flat shaping of the suspended part 30 ensures a precise handling during introduction and removal and prevents any laceration of the very sensitive iris.

The free, arcuate portion 36 of the suspended part 30 can preferably be adapted to the not shown shape of the outer contour of the eye 10 (sclera), so that the operating area is readily accessible.

For handling purposes in the end region of the arcuate portion 36, the suspended part 30 is provided with not shown grooving, notching, etc. by means of which optimum handling and positioning is ensured.

The suspended part 30 can be made from stainless steel, e.g. a suitable chrome-nickel spring steel (X 12 Cr.Ni 17 7; according to DIN 17224). The use of a magnetized chrome-nickel steel for producing the suspended part 30 offers the advantage that the relatively small suspended part can be more easily removed from the operating area. The dimensions of the suspended part 30 are approximate length 6 to 8 mm, approximate width 4 mm and approximate thickness 0.25 mm.

However, the suspended part 30 can also be made from a suitable plastics material, in which the hook portion 31 for gripping and holding the iris is constructed with an adequate stiffness and the guide part 35 for adapting to the outer contour of the eye 10 (sclera) is made relatively flexible. Through a corresponding flexibility of the plastics material used, it is possible to substantially exclude any injury risk of the interior of the eye 10 due to unintentional contact of the projecting element. The suspended part 30 made from a suitable plastics material can also easily be adapted to the outer shape of the eye, which also prevents unintentional contact.

In the case of the suspended part 30' made from a suitable plastics material and partly shown in FIG. 6, it is possible to provide the plastics suspended part 30' with a hook portion 31' made from a stainless steel material, e.g. chrome-nickel spring steel (X 12 Cr.Ni 17 7; according to DIN 17224). In an appropriate manner the hook portion 31 is embedded in the front portion 34' of the suspended part 30'.

FIG. 8 is a diagrammatic plan view of a portion of the eye 10 with the iris region 12" retracted by means of an iris retractor 20'. In this embodiment two spaced suspended parts 30 or 30' are provided on a clamping part 25". The latter essentially corresponds to the clamping part 25 according to FIG. 3 and is provided with corresponding spaced recesses 26, 26' and openings 27. Diverging from the construction according to FIG. 3, the clamping part 25" according to FIG. 8 is constructed as an arcuate segment and comprises two spaced suspended parts 30 or 30'.

FIG. 9 is a diagrammatic plan view of the eye 10 and it is possible to see a plurality of iris retractors 20 distributed for the opening of the pupil 14' (FIG. 1). The suspended part 30 grips and holds the iris region and draws it roughly radially outwards. The clamping part 25 located on the suspended part 30 and displaceable in arrow direction R holds the iris retractor 20 fixing the iris region at the transition 15.

We claim:

1. An iris retractor for use when operating on an eye of a living creature, said iris retractor comprising:
   a suspended part having a hook portion bent over once in a hairpin-like manner for retracting the iris and a guide portion comprising a straight portion and bent portion, said suspended part having a rod-like profile body with at least two parallel, spaced, longitudinally oriented guide faces arranged orthogonally thereto and adapted to pass through the cornea at a transition region between the sclera and cornea of the eye; and
   a platelet-like clamping-part for positioning and fixing said suspended part at said transition region between the sclera and cornea, said clamping part having a rectangular profile cross-section with a slot-like opening for receiving said suspended part and at least one recess for adaptation of said clamping-part to said transition region.

2. An iris retractor according to claim 1, wherein said suspended part is constructed from stainless steel.

3. An iris retractor according to claim 2, wherein the stainless steel is a chrome-nickel steel.

4. An iris retractor according to claim 1, wherein said hook portion is constructed from chrome-nickel steel and said guide portion is constructed from a flexible plastics material.

5. An iris retractor according to claim 4, wherein said flexible plastics material is silicone rubber.

6. An iris retractor according to claim 1, wherein said platelet-like clamping part is constructed from a flexible plastics material.

7. An iris retractor according to claim 6, wherein said flexible plastics material is silicone rubber.

8. An iris retractor according to claim 7, wherein said platelet-like clamping part comprises at least two slot-like openings for positioning and fixing at least two suspended parts.

9. An iris retractor according to claim 7, wherein said platelet-like clamping part comprises two accurate recesses which ensure adaptation to said transition region.

10. An iris retractor according to claim 7, wherein said platelet-like clamping part comprises a single central recess being connected to two openings oriented in the longitudinal direction.

* * * * *